(12) United States Patent
Freyman et al.

(10) Patent No.: US 7,972,295 B2
(45) Date of Patent: Jul. 5, 2011

(54) APPARATUS AND METHODS FOR DELIVERING A BOLUS OF THERAPEUTIC MATERIAL

(75) Inventors: Toby Freyman, Waltham, MA (US); Inas Khayal, San Francisco, CA (US); Wendy Naimark, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1840 days.

(21) Appl. No.: 11/077,117

(22) Filed: Mar. 11, 2005

(65) Prior Publication Data

US 2006/0217656 A1 Sep. 28, 2006

(51) Int. Cl.
*A61M 31/00* (2006.01)
(52) U.S. Cl. ........................................ 604/57
(58) Field of Classification Search ............... 604/140, 604/256, 57, 59, 60, 14
See application file for complete search history.

(56) References Cited

U.S. PATENT DOCUMENTS

| | | | |
|---|---|---|---|
| 4,994,028 A | 2/1991 | Leonard et al. | |
| 5,030,210 A * | 7/1991 | Alchas | 604/247 |
| 5,167,624 A | 12/1992 | Butler et al. | |
| 5,222,939 A | 6/1993 | Tiefenbrun et al. | |
| 5,288,291 A | 2/1994 | Teoh | |
| 5,484,403 A | 1/1996 | Yoakum et al. | |
| 6,142,972 A | 11/2000 | Cheikh | |
| 6,238,406 B1 | 5/2001 | Ellis et al. | |
| 6,290,980 B1 | 9/2001 | Hansen | |
| 6,299,590 B1 | 10/2001 | Luscher et al. | |
| 6,436,068 B1 | 8/2002 | Bardy | |
| 6,689,089 B1 * | 2/2004 | Tiedtke et al. | 604/43 |
| 2003/0015203 A1 | 1/2003 | Makower et al. | |

FOREIGN PATENT DOCUMENTS

| | | |
|---|---|---|
| EP | 0934729 A2 | 8/1999 |
| WO | WO 00/72908 A1 | 12/2000 |
| WO | WO 2004/098420 A1 | 11/2004 |

OTHER PUBLICATIONS

International Search Report dated Jun. 26, 2006, for PCT International Application No. PCT/US2006/003307, 4 pages.

* cited by examiner

*Primary Examiner* — Kevin C Sirmons
*Assistant Examiner* — Deanna K Hall
(74) *Attorney, Agent, or Firm* — Seager, Tufte & Wickhem LLC (57) ABSTRACT

Apparatus and method utilizing fluid to deliver a bolus of therapeutic material through a lumen to a delivery or discharge control portion of the apparatus, where the bolus may be discharged or delivered to a desired location.

36 Claims, 5 Drawing Sheets

APPARATUS AND METHODS FOR DELIVERING A BOLUS OF THERAPEUTIC MATERIAL

BACKGROUND OF THE INVENTION

This invention relates generally to catheters, and more particularly, to a catheter for delivering a bolus of therapeutic materials to tissue to be treated.

There are many instances in which it is desirable to deliver a therapeutic material to a target location, such as directly to tissue to be treated by the therapeutic material. It is often desirable, or unavoidable, that the therapeutic material be in the form of a bolus, rather than liquid form. Known techniques for delivering liquid therapeutic materials are often not useful for delivering boluses of therapeutic materials. Moreover, many known techniques for delivering boluses of therapeutic material require complicated delivery devices or have disadvantages and limitations that render then unsuitable for some applications.

SUMMARY OF EMBODIMENTS OF THE INVENTION

The disclosed embodiments of methods and apparatuses strive to address some of the disadvantages and limitations of known techniques for delivering boluses of therapeutic materials. The described embodiments employ fluid to transport a bolus of therapeutic material through a lumen to a delivery or discharge control portion of the apparatus and optionally to discharge or deliver the bolus. In some embodiments the apparatus has a second lumen into which fluid from the first lumen is discharged in connection with transporting the bolus. In some embodiments the delivery or discharge control portion of the apparatus includes a valve or other obstruction by which the bolus is selectively retained until it is to be delivered or discharged.

DETAILED DESCRIPTION OF THE INVENTION

The various embodiments of apparatuses and methods disclosed below are for the delivery of one or more therapeutic materials. The therapeutic material can be delivered to any desired location, typically internal to a human or other body. In one embodiment, the therapeutic material is delivered into a body cavity or deposited or inserted into an organ or other tissue. Exemplary applications are delivery or implantation of therapeutic material into the myocardium or prostate.

As used herein, the terms "therapeutic agent," "therapeutic material," "active material," and similar terms includes, but is not limited to, any therapeutic agent or active material, such as drugs, genetic materials, and biological materials. Suitable genetic materials include, but are not limited to, DNA or RNA, such as, without limitation, DNA/RNA encoding a useful protein, DNA/RNA intended to be inserted into a human body including viral vectors and non-viral vectors, and RNAi (RNA interfering sequences). Suitable viral vectors include, for example, adenoviruses, gutted adenoviruses, adeno-associated viruses, retroviruses, alpha viruses (Semliki Forest, Sindbis, etc.), lentiviruses, herpes simplex viruses, ex vivo modified and unmodified cells (e.g., stem cells, fibroblasts, myoblasts, satellite cells, pericytes, cardiomyocytes, skeletal myocytes, macrophage), replication competent viruses (e.g., ONYX-015), and hybrid vectors. Suitable non-viral vectors include, for example, artificial chromosomes and mini-chromosomes, plasmid DNA vectors (e.g., pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD).

Suitable biological materials include, but are not limited to, cells, yeasts, bacteria, proteins, peptides, cytokines, and hormones. Examples of suitable peptides and proteins include growth factors (e.g., FGF, FGF-1, FGF-2, VEGF, Endothelial Mitogenic Growth Factors, and epidermal growth factors, transforming growth factor $\alpha$ and $\beta$, platelet derived endothelial growth factor, platelet derived growth factor, tumor necrosis factor $\alpha$, hepatocyte growth factor and insulin-like growth factor), transcription factors, proteinkinases, CDK inhibitors, thymidine kinase, and bone morphogenic proteins (BMP's), such as BMP-2, BMP-3, BMP-4, BMP-5, BMP-6 (Vgr-1), BMP-7 (OP-1), BMP-8. BMP-9, BMP-10, BMP-11, BMP-12, BMP-13, BMP-14, BMP-15, and BMP-16. Currently preferred BMP's are BMP-2, BMP-3, BMP-4, BMP-5, BMP-6, and BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at a desired site. The delivery media can be formulated as needed to maintain cell function and viability. Cells include, for example, whole bone marrow, bone marrow derived mono-nuclear cells, progenitor cells (e.g., endothelial progenitor cells), stem cells (e.g., mesenchymal, hematopoietic, neuronal), pluripotent stem cells, fibroblasts, macrophage, and satellite cells.

The term "therapeutic agent" and similar terms also includes non-genetic agents, such as: anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid, amlodipine and doxazosin; anti-inflammatory agents such as glucocorticoids, betamethasone, dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives; anesthetic agents such as lidocaine, bupivacaine, and ropivacaine; anti-coagulants such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides; vascular cell growth promotors such as growth factors, Vascular Endothelial Growth Factors (VEGF, all types including VEGF-2), growth factor receptors, transcriptional activators, Insulin Growth Factor (IGF), Hepatocyte Growth Factor (HGF), and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents, vasodilating agents, and agents which interfere with endogenous vasoactive mechanisms; anti-oxidants, such as probucol; antibiotic agents, such as penicillin, cefoxitin, oxacillin, tobranycin; angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril.

Preferred therapeutic materials include anti-proliferative drugs such as steroids, vitamins, and restenosis-inhibiting agents such as cladribine. Preferred restenosis-inhibiting agents include microtubule stabilizing agents such as Taxol, paclitaxel, paclitaxel analogues, derivatives, and mixtures thereof. For example, derivatives suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt. Other preferred therapeutic materials include nitroglycerin, nitrous oxides, antibiotics, aspirins, digitalis, and glycosides.

As described above, the present invention relates to the delivery of boluses of therapeutic material. A bolus is a non-fluid mass of one or more therapeutic materials. For example, a solid or semi-solid mass of one or more therapeutic agents. The bolus may be formed entirely of one or more therapeutic agents or may be carried, combined, or mixed with other materials. In one embodiment, the bolus is in the form of a solid pellet or plug formed in a shape compatible with delivery via the disclosed catheter lumen. For example, in some embodiments, the bolus is cylindrical, ovular or cubic. In one embodiment, the bolus is sufficiently large that it sealingly, slidably, engages the interior wall of the lumen or can be smaller. In another embodiment, the bolus is small enough such that it does not sealingly, slidably engage the interior wall of the lumen. The bolus may also include a coating or encapsulating outer layer. Such a layer can help maintain the integrity of the bolus during transport through the delivery lumen and passage through the discharge control mechanism. The layer can also inhibit attachment of the bolus to the lumen wall and subsequent distortion or smearing of the bolus along the lumen wall. An encapsulating layer could be formed of a biocompatible/biodegradable polymer material.

Figure 1:
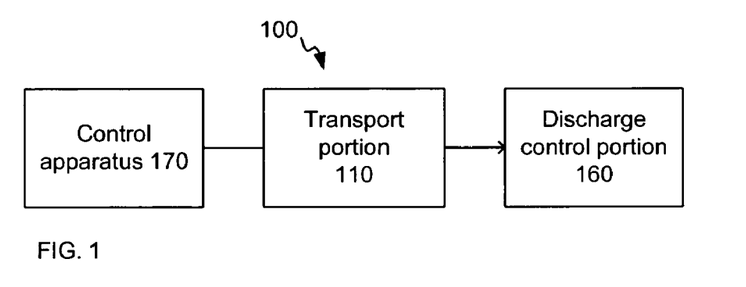
FIG. 1 is a schematic illustration of an apparatus for delivering a bolus of therapeutic material in accordance with one embodiment of the present invention.

A generic representation of a catheter 100 incorporating the principles of the invention is illustrated schematically in FIG. 1. Catheter 100 includes a transport portion 110, and can optionally include a delivery or discharge control portion 160. Transport portion 110 uses fluid to transport one or more boluses of therapeutic material to a distal end of the catheter. Delivery or discharge control portion 160 controls the delivery or discharge of one or more boluses from transport portion 110. Control apparatus 170 may be coupled to catheter 100 to supply fluid to and/or remove fluid from transport portion 110, to monitor fluid pressure in transport portion 110, and to provide any other desired catheter control functions.

Figure 2:
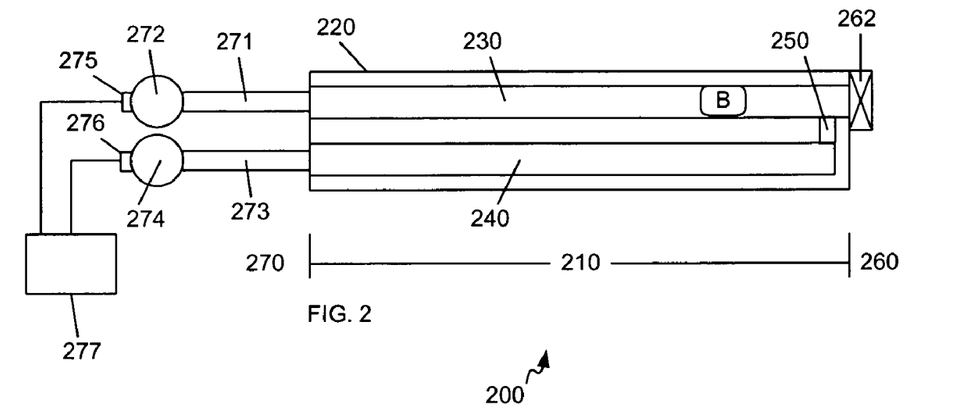
FIG. 2 is a schematic illustration of another apparatus for delivering a bolus of therapeutic material in accordance with one embodiment of the present invention.

A first embodiment of catheter 200 is illustrated schematically in FIG. 2. Transport portion 210 includes a catheter body 220, which may be of any conventional catheter construction. Catheter body 220 has two internal lumens—a delivery lumen 230 and a fluid return lumen 240. Delivery lumen 230 is sized to accommodate a bolus B of therapeutic material having a desired circumference or cross-sectional area. In the illustrated embodiment, the bolus B and delivery lumen 230 are sized and have cross-sectional shapes such that the bolus B sealingly engages the internal surface of the lumen 230. Lumens 230, 240 are fluidically coupled near the distal end of catheter body 220 by a connecting channel 250, which may be in the form of a conduit, port, or other passage for communicating fluid between lumens 230, 240.

Discharge control portion 260 is disposed at the distal end of catheter body 220, and includes a valve 262 disposed at the distal end of delivery lumen 230. Valve 262 may be any suitable one-way, pressure-responsive, or other similar valve. Valve 262 is normally closed, and thus obstructs or closes the distal end of delivery lumen 230. Valve 262 is also configured to open (and permit bolus B to be discharged from delivery lumen 230 and pass through the valve). Hence, valve 262 is sized to permit bolus B to pass through the valve when it is open. In this embodiment, valve 262 is configured to open in response to a predetermined differential between the pressure of fluid in delivery lumen 230 (on the lumen side of the valve) and the ambient pressure (on the opposite side of the valve).

Control apparatus 270 includes a first fluid source 272 and a second fluid source 274, as well as a fluid supply line 271 coupling first fluid source 272 to the proximal end of delivery lumen 230 and a fluid return line 273 coupling second fluid source 274 to the proximal end of fluid return lumen 240. In the illustrated embodiment, fluid sources 272, 274 are instrumented with pressure sensors 275, 276 to detect the pressure of fluid provided by the sources, and are automatically regulated by a control system 277 (which may be a programmable pressure control system) such that each source is capable of establishing and maintaining selected fluid pressures. In an alternative embodiment, the pressure is manually regulated by an operator of catheter 200. The fluid sources, fluid supply lines, and control system function to circulate the fluid through the lumens and channel, which together form a fluid passage.

The operation of catheter 200 and control apparatus 270 to deliver or discharge bolus B is described below with reference to FIGS. 2 and 3A-3C. Transport portion 210 is filled with fluid, so that delivery lumen 230, fluid return lumen 240, and connecting channel 250 contain fluid. In one embodiment, transport portion 210 is filled with fluid and one or more boluses prior to use. The fluid is preferably a liquid, such as water or saline and blood. Other bio-compatible fluids could be selected based on their density, viscosity and other properties depending on the properties of the bolus, e.g., a low-density fluid for a high-viscosity bolus, a high-density fluid for a low-viscosity bolus, etc. Blood (whole blood or plasma)

may also be used as the fluid, such as in instances where the bolus is composed of a material that needs to be kept in blood or a blood-like fluid. The fluid could also be a gas, such as $CO_2$ or air, or a combination of liquids and gases. Bolus B is disposed in delivery lumen 230 near the proximal end of catheter 200. Valve 230 is closed. Catheter 200 is introduced into the body of a subject to be treated, and the distal end is inserted into tissue to be treated with the therapeutic agent contained in bolus B (such as myocardial tissue).

First fluid source 272 and/or second fluid source 274 increases the pressure (P1) in fluid supply line 271 with respect to a pressure (P2) in fluid return line 273. The difference between pressure P1 and P2 produces a pressure differential across bolus B, because fluid in delivery lumen 230 on the proximal side of bolus B is at pressure P1, while fluid in fluid return lumen 240, connecting channel 250, and delivery lumen 230 on the distal side of bolus B is at pressure P2. When the force produced on bolus B by the fluid pressure differential exceeds the frictional forces between the outer surface of bolus B and the inner surface of delivery lumen 230, bolus B begins to move distally along delivery lumen 230.

Figure 3A:
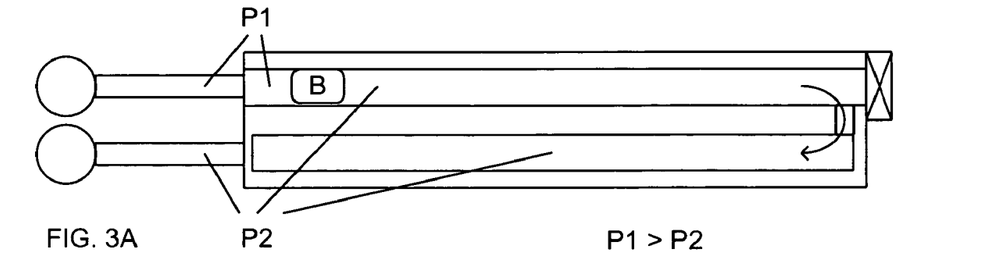
FIGS. 3A-3C are schematic illustrations of the operation of the apparatus of FIG. 2 to deliver a bolus of active material.

As bolus B moves along delivery lumen 230, fluid on the distal side of bolus B is displaced through channel 250 into return lumen 240 and toward second fluid source 273, as shown by the arrow in FIG. 3A.

Figure 3B:
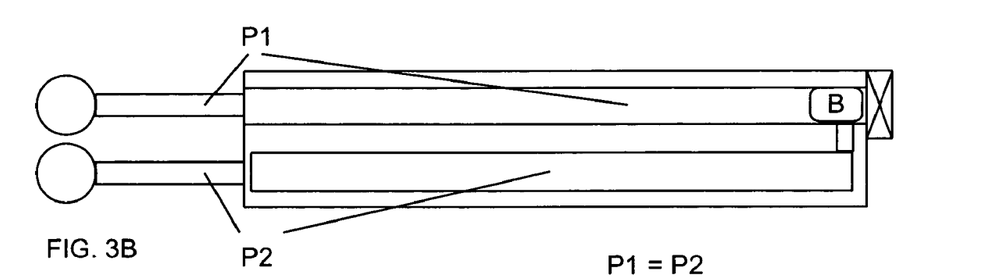

As bolus B reaches the distal end of delivery lumen 230, it blocks channel 250 (as shown in FIG. 3B), preventing or decreasing volumetric discharge of fluid from portion of delivery lumen 230 distal to bolus B. This will produce a detectable change in pressure P1 and/or P2, and/or the rate of fluid flow into delivery lumen 230 and/or out of return lumen 240. Control apparatus 270 can thus determine that bolus B is at the distal end of delivery lumen 230 and therefore positioned adjacent valve 262.

Figure 3C:
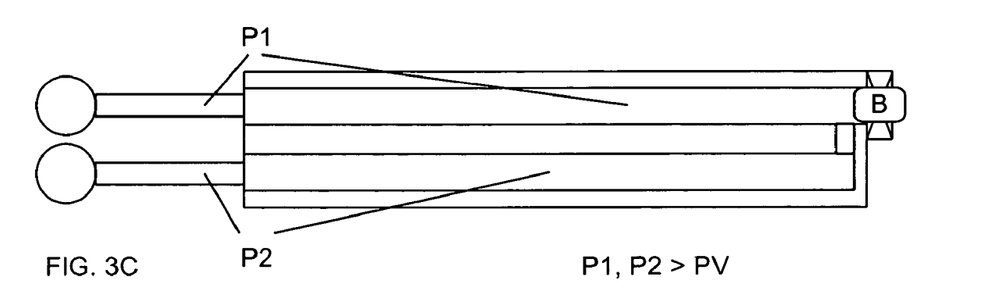

Pressures P1 and P2 are both increased so that the pressure exerted by bolus B (and/or by any fluid remaining in delivery lumen 230 between bolus B and valve 262) on valve 262 exceeds the opening pressure threshold for valve 262. Then, as shown in FIG. 3C, bolus B passes through valve 262 into the tissue or body lumen or cavity external to valve 262. The discharge of bolus B will quickly reduce the fluid pressure in the delivery lumen adjacent valve 262, which will then close, preventing discharge of excessive fluid. In addition to producing a detectable change in pressure P1 and/or P2, the discharge of bolus B may also produce a detectable change in the rate of fluid flow into delivery lumen 230 and/or out of return lumen 240. Control apparatus 270 can thus determine that bolus B has been discharged and accordingly reduce pressures P1 and P2.

Pressures P1 and P2 can be of any appropriate desired values during the operation of the catheter, and each may be higher or lower than the ambient pressure external to the catheter (provided that they need to be higher than the pressure external to valve 262 when discharging bolus B). Suitable pressures may be between 100-400 psi, although pressures may vary beyond this range depending on the liquid used, the dimensions of the lumen, and the properties of the bolus.

Figure 4A:
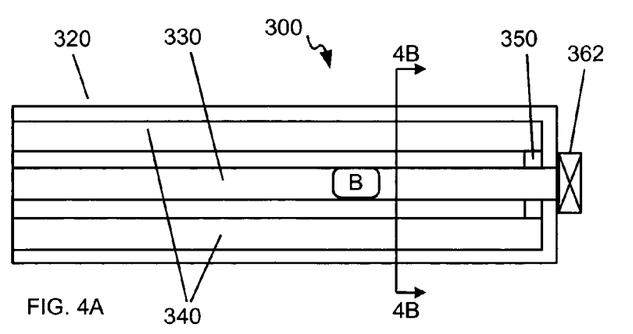
FIG. 4A is a schematic illustration of an alternative embodiment of a catheter usable with the apparatus of FIG. 2.
Figure 4B:
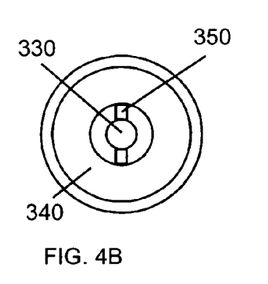
FIG. 4B is a cross-sectional schematic illustration of the catheter of FIG. 4A taken along line 4B-4B.

There are many possible variations on the construction of the catheter, including the geometry and arrangement of the lumens. One example of an alternative catheter 300 is illustrated schematically in FIGS. 4A and 4B. Catheter body 320 is formed with a central delivery lumen 330 and an annular fluid return lumen 340 disposed concentrically about delivery lumen 330. Channels 350 fluidically couple lumens 330, 340 at their distal ends. Valve 362 is disposed at the distal end of delivery lumen 330. Operation of the catheter of this embodiment is similar to that of catheter 200 above.

Figures 5A, 5B, 5C, 5D:
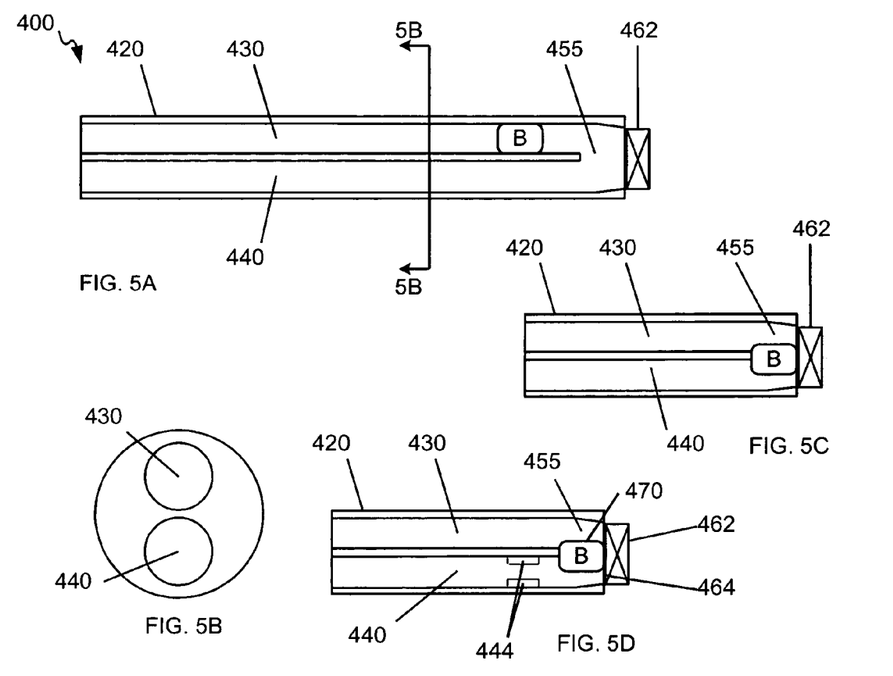
FIG. 5A is a schematic illustration of an alternative embodiment of a catheter usable with the apparatus of FIG. 2.
FIG. 5B is a cross-sectional schematic illustration of the catheter of FIG. 5A taken along line 5B-5B.
FIG. 5C is a further schematic illustration of the embodiment of FIG. 5A.
FIG. 5D is a schematic illustration of a further alternative embodiment of a catheter usable with the apparatus of FIG. 2.

Another alternative catheter 400 is illustrated schematically in FIGS. 5A-5C. In this embodiment, catheter body 420 is formed with delivery lumen 430 and fluid return lumen 440 arranged in parallel, and terminating at their distal end in a chamber 455. Valve 462 is disposed at the distal end of chamber 455. Chamber 455 is sized to accommodate bolus B therein, adjacent to valve 462 (as shown in FIG. 5C), preparatory to discharging bolus B. Operation of the catheter of this embodiment is similar to that of catheter 200 above.

Another alternative catheter 400, similar to the catheter 400 of FIGS. 5A-5C, is illustrated schematically in FIG. 5D. In this embodiment electrostatic charges are use to inhibit passage of bolus B down fluid return lumen 440. Bolus B includes a charged outer layer 470. Layer 470 can be positively or negatively charged. Valve 462 or a portion 464 proximate to valve 462 is charged oppositely to charged layer 470 of bolus B to attract bolus B to valve 462. Fluid return lumen 440 may also include portions 444 having the same charge as charged layer 470 to further inhibit bolus B from traveling down fluid return lumen 440.

Figure 6A:
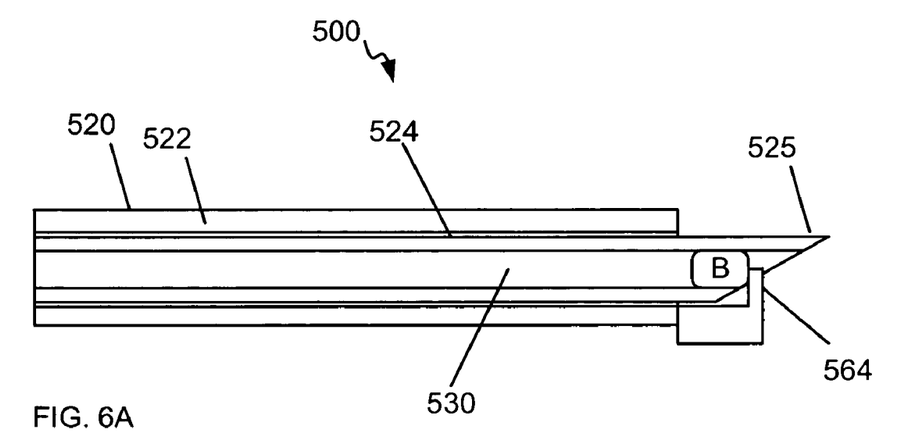
FIGS. 6A-6B are schematic illustrations of an alternative embodiment of a catheter.
Figure 6B:
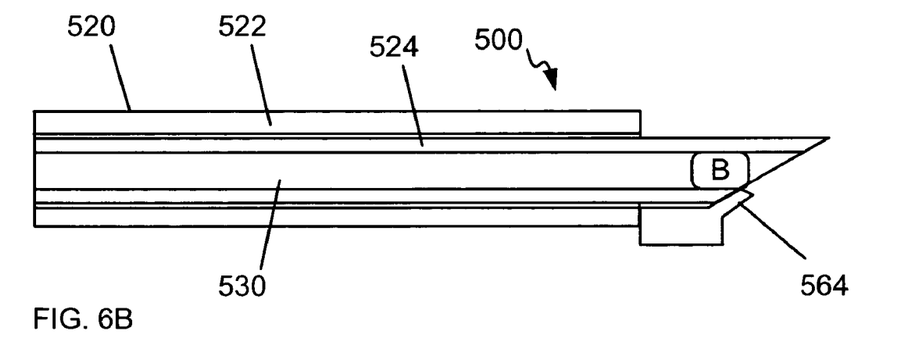

FIGS. 6A and 6B illustrate another alternative catheter 500, which employs only one lumen 530 for fluid delivery of the bolus. Catheter body 520 has an outer canula 522 and an inner canula 524 that are moveable with respect to each other. Delivery lumen 530 is disposed within inner canula 524. The distal end 525 of inner canula 524 is sharpened, so that it can pierce tissue. Inner canula 525 is thus essentially a needle.

An obstruction 564 is disposed at, and coupled to, outer canula 522. Obstruction 564 extends into a position blocking the distal end of delivery lumen 530. Obstruction 564 thus controls the discharge of bolus B from delivery lumen 530 when the canulas 522, 524 are positioned as shown in FIG. 6A.

When the two canulas 522, 524 are moved into a relative position illustrated in FIG. 6B in which inner canula 524 extends outwardly from outer canula 522, the obstruction 564 is displaced away from the distal end of delivery lumen 530 so that it no longer prevents the discharge of the bolus B from lumen 530. Relative movement of the two canulas 522, 524 can be achieved by any number of known manual or automatic devices, such as a linear displacement transducer.

Obstruction 564 can be formed of any suitable resilient material so that it can be deformed or deflected out of the blocking position. Alternatively, obstruction 564 can be constructed from rigid material in two relatively movable portions, so that the portion blocking delivery lumen 130 can be displaced by moving relative to the other portion.

The operation of the delivery catheter incorporating catheter body 520 is similar to that of the other embodiments above, except that there is not a fluid discharge lumen. Thus, bolus B is urged through and along delivery lumen 530 by pressurized fluid in delivery lumen 530 on the proximal side of bolus B. Any fluid in delivery lumen 530 on the distal side of bolus B would be expelled through the distal end of delivery lumen 530.

The needle and obstruction structures of this embodiment could also be used as the discharge control mechanism for the catheter of FIG. 2, i.e. in place of valve 262. This combination is illustrated schematically in FIG. 7. The transport portion includes a catheter body 620 with a canula 624 protruding from the distal end. Canula 624 terminates in a sharpened end 625. Delivery lumen 630 passes through catheter body 620 and canula 624. Catheter body 620 also includes a fluid return lumen 640. The lumens are fluidically coupled near the distal end of catheter body 620 by a connecting channel or port 650.

Figure 7:
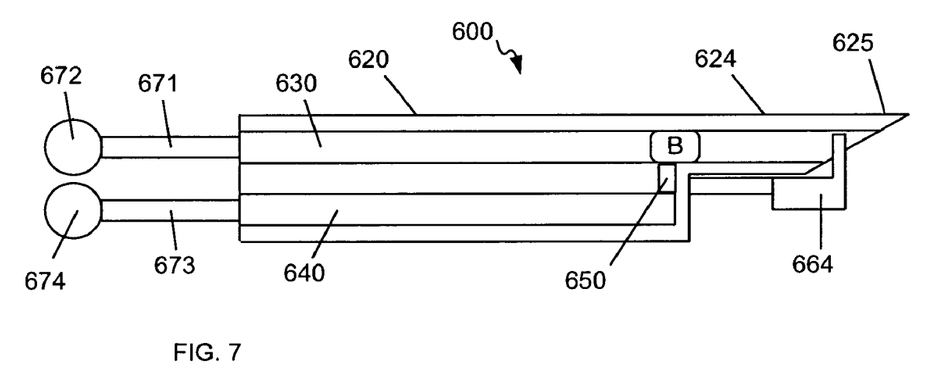
FIG. 7 is a schematic illustration of another apparatus for delivering a bolus of active material.

Sharpened end 625 and obstruction 664 form the discharge control portion. Obstruction 664 is mounted to catheter body 620 for movement with respect to end 625. In this embodiment, a portion of obstruction 664 may fluidically seal the distal end of delivery lumen 630 to prevent discharge of fluid contained in delivery lumen 630 as bolus B is displaced through the lumen. Until bolus B passes port 650, fluid on the distal side of bolus B can be displaced into fluid return lumen 640.

Control apparatus 670 includes first fluid source 672 and second fluid source 674, as well as fluid supply line 671 coupling first fluid source 672 to the proximal end of delivery lumen 630 and fluid return line 673 coupling second fluid source 672 to the proximal end of fluid return lumen 640. As with the embodiment of FIG. 2, the fluid sources may be instrumented with pressure sensors to detect the pressure of fluid provided by the sources, and are preferably regulated such that each source is capable of establishing and maintaining selected fluid pressures.

In operation, sharpened end 625 may be inserted into tissue into which bolus B is to be delivered. Bolus B can be fluidically transported through delivery lumen 630 by differential fluid pressures in the two lumens until it reaches port 650. Obstruction 664 may then be moved with respect to canula 624 so that it is not obstructing the distal end of delivery lumen 630. The pressure in both lumens can then be increased to displace bolus B through the remainder of delivery lumen 630 and out of the distal end thereof into the tissue.

The embodiments are described with a single bolus B disposed in the delivery lumen. The artisan will recognize that the delivery lumen may be loaded with multiple boluses. All of the boluses would be transported along the delivery lumen until the most distal bolus reaches the discharge control mechanism. The most distal bolus would delivered as described above, and then the series of boluses would be further transported through the delivery lumen until the next bolus reaches the discharge control mechanism.

Alternatively, or in addition, a supply of boluses can be coupled to the proximal end of delivery lumen to selectively or automatically introduce additional boluses into the delivery lumen.

In the embodiments disclosed above, the bolus is described as sealingly engaging the inner wall of the delivery lumen. In such cases, fluid flows through the delivery lumen only in connection with movement of the bolus (at least unless or until the bolus passes to the distal side of any port or passage fluidically coupling the delivery lumen to the fluid return lumen). Further, a pressure differential can be established across the bolus (to provide a motive force to urge the bolus through the delivery lumen) hydrostatically, i.e. without fluid flow. However, it is not necessary for the bolus to sealingly engage the delivery lumen wall. If the bolus is smaller than the delivery lumen, such that fluid can flow around the bolus, the bolus can be entrained in the fluid flow, urged along the delivery lumen by dynamic fluid pressure forces. A smaller bolus can thus be transported through the delivery lumen at least to the location of the port of passage that fluidically couples the lumens (since the fluid flow that entrains the bolus will pass through the port). The passage or passages should be sized (this is just multiple passages) to prevent the bolus from entering the fluid return lumen. The fluid flow rates and/or pressures in one or both of the two lumens should change in a detectable way when the bolus reaches the port or passage so that the control system can then adjust the pressure in the two lumens to move the bolus to and through the discharge control mechanism, as described above.

In some embodiments above, the valve of the discharge control mechanism is disclosed as opening in response to pressure. Alternatively, the valve or other mechanism by which the bolus and/or fluid is prevented from being discharged from the delivery lumen can be opened by other means, such as mechanically, electronically, or magnetically, such as in response to a control signal supplied by the control system. As a further alternative, the discharge control mechanism could include a single-use mechanism rather than a multiple-use valve. For example, a frangible diaphragm could be used. The diaphragm would rupture upon application of a predetermined pressure differential between the pressure of fluid in the delivery lumen (on the lumen side of the diaphragm) and the ambient pressure (on the opposite side of the diaphragm).

While the invention has been described in detail and with reference to specific embodiments thereof, it will be apparent to one skilled in the art that various changes and modifications may be made therein without departing from the spirit and scope thereof. Thus, it is intended that the present invention covers the modifications and variations of this invention provided they come within the scope of the appended claims and their equivalents.

What is claimed is:

1. A catheter assembly comprising:
   a lumen having a distal end and a proximal end;
   a bolus of therapeutic material slidably and sealingly engaged within said lumen; and
   a source of pressurized fluid coupled to said proximal end of said lumen,
   whereby introduction of pressurized fluid from said source of pressurized fluid into said proximal end of said lumen displaces said bolus toward said distal end of said lumen.

2. The catheter assembly of claim 1, further comprising a discharge control device in fluidic communication with said distal end of said lumen, said discharge control device being adapted to permit passage of the bolus therethrough in response to application of a predetermined fluid pressure in said lumen.

3. The catheter assembly of claim 1, wherein said lumen is a first lumen, said catheter further comprising a second lumen, said second lumen having a distal end fluidically coupled to said first lumen proximate said distal end of said first lumen to permit discharge of fluid from said first lumen into said second lumen.

4. The catheter assembly of claim 1, wherein said bolus is a solid plug.

5. An apparatus for conveying a bolus of a therapeutic material, comprising:
   an elongate body having a distal end;
   a supply lumen disposed in said body for receiving fluid; and
   a return lumen disposed in said body for outputting fluid, said supply lumen and said return lumen being in fluidic communication with each other proximate to said distal end of said body, said supply lumen being configured to receive the bolus for conveyance therethrough, said supply lumen and said return lumen being configured such that the bolus is conveyed along said supply lumen when fluid is delivered from said supply lumen to said return lumen.

6. The apparatus of claim 5, further comprising a mechanism for controlling discharge of the bolus from said body.

7. The apparatus of claim 6, wherein said mechanism for controlling discharge of the bolus includes a normally-closed valve which opens sufficiently in response to a predetermined fluid pressure in said supply lumen to permit passage of the bolus through said valve.

8. The apparatus of claim 6, further including a chamber disposed in said catheter adjacent said mechanism for controlling discharge, said chamber coupled to said distal end of said supply lumen and to said distal end of said return lumen to provide fluidic communication between said lumens, said chamber adapted to accommodate the bolus adjacent to said mechanism for controlling discharge.

9. The apparatus of claim 5, further including a bolus of an active agent disposed in said supply lumen.

10. The apparatus of claim 9, wherein said bolus slidably engages said supply lumen.

11. Apparatus for delivering a bolus of a therapeutic material, comprising:
    a catheter;
    a lumen disposed in said catheter, having a distal end and a proximal end, and being adapted to allow passage of the bolus therethrough; and
    a discharge control device in fluidic communication with said distal end of said lumen, said discharge control device being adapted to permit passage of the bolus therethrough in response to application of a predetermined fluid pressure in said lumen.

12. The apparatus of claim 11, further comprising a source of pressurized fluid fluidically coupled to said proximal end of said lumen and adapted to supply fluid to said lumen at a range of pressures including said predetermined fluid pressure.

13. The apparatus of claim 11, wherein said lumen is a first lumen and further comprising a second lumen disposed in said catheter, said second lumen having a distal end fluidically coupled to said first lumen proximate said distal end of said first lumen to permit discharge of fluid from said first lumen into said second lumen.

14. The apparatus of claim 13, wherein said source of pressurized fluid is a first source of pressurized fluid and further comprising a second source of pressurized fluid fluidically coupled to said proximal end of said second lumen.

15. The apparatus of claim 12, further comprising means for measuring the pressure of fluid in said first lumen.

16. The apparatus of claim 11, further comprising a bolus of bioactive material disposed in said lumen.

17. The apparatus of claim 16, wherein said bolus is slidingly sealingly engaged with said lumen.

18. A catheter for discharging a bolus of therapeutic material, comprising:
    a fluid passage formed in said catheter body and extending from a proximal end of said catheter body, to a distal end of said catheter body, and back to said proximal end of said catheter body;
    means for circulating fluid through said passage; and
    a normally-closed valve at said distal end of said catheter, said valve being selectively openable to permit fluidic communication between said passage and the exterior environment of said catheter,
    whereby a bolus disposed in said passage can be transported toward said valve by fluid circulated in said passage.

19. The catheter of claim 18, said valve opening in response to application of pressure exceeding a predetermined threshold value.

20. A method of delivering a bolus of therapeutic material via a catheter having an internal lumen, the bolus being disposed in the lumen, the lumen containing fluid on a distal side and a proximal side of the bolus, said method comprising:
    creating a differential in the pressure of the fluid in the lumen across the bolus, the pressure of the fluid on the distal side of the bolus being lower than the pressure of the fluid on the proximal side of the bolus, said pressure differential displacing the bolus through the lumen toward a distal end of the catheter.

21. The method of claim 20, wherein the bolus sealingly engages the interior wall of the lumen.

22. The method of claim 20, wherein the pressure on the distal side of the bolus is greater than the pressure external to the catheter.

23. The method of claim 20, wherein the lumen is a first lumen and the catheter further includes a second lumen and a channel that fluidly couples the first and second lumens, said creating a differential in pressure including forcing fluid from the first lumen into the second lumen via the channel.

24. The method of claim 23,
    further comprising at least one of (1) detecting a change in the pressure of the fluid in at least one of the first and second lumens and (2) directing a change in volumetric fluid flow in at least one of the first and second lumens.

25. The method of claim 24, further comprising discharging the bolus from the distal end of the catheter and wherein said discharging the bolus is performed after said detecting.

26. The method of claim 20, further comprising discharging the bolus from the distal end of the catheter and wherein said discharging the bolus includes causing a valve of the catheter to open.

27. The method of claim 26, wherein the valve is configured to open in response to a predetermined pressure differential between the fluid on the lumen side of the valve, said causing the valve to open including increasing the pressure differential between the lumen side of the valve and the pressure external of the valve.

28. The method of claim 20, wherein the fluid is a liquid.

29. A method of delivering a bolus of therapeutic material via a catheter having a supply lumen and a return lumen, the bolus being disposed in the supply lumen, the return lumen fluidically communicating with the supply lumen proximate to a distal end of the catheter, the supply lumen containing fluid on a distal side and a proximal side of the bolus, said method comprising:
    supplying pressurized fluid to said supply lumen proximal to said bolus and displacing fluid from the supply lumen distal to the bolus into the return lumen to displace the bolus through the supply lumen.

30. The method of claim 29, further comprising discharging the bolus from the distal end of the catheter.

31. The method of claim 30, wherein said discharging the bolus includes establishing a pressure in the fluid on the proximal side of the bolus greater than the pressure external to the distal end of the catheter.

32. A method of delivering a bolus of therapeutic material via a catheter having an internal lumen, the bolus being disposed in the lumen, the lumen containing fluid on a distal side of the bolus, the catheter having an obstruction selectively disposed to inhibit discharge of the bolus from a distal end of the lumen, said method comprising:
    supplying fluid to the lumen proximal to the bolus;
    displacing the bolus to the distal end of the lumen;
    displacing the obstruction to permit discharge of the bolus from the distal end of the lumen.

33. The method of claim 32, wherein the bolus engages the interior wall of the lumen.

34. The method of claim 32, wherein the catheter includes a fluid relief passage having a distal end in fluidic communication with the lumen near the distal end of the lumen, the lumen having fluid therein on the distal side of the bolus, and wherein said displacing the bolus includes discharging fluid from the lumen into the fluid relief passage.

35. The method of claim 32, wherein the obstruction is a valve selectively fluidically isolating the distal end of the lumen from the exterior of the catheter, the valve opening in response to a predetermined pressure differential between the fluid on the lumen side of the valve and the pressure external to the valve and wherein said displacing the obstruction includes establishing a pressure in the fluid on the proximal side of the bolus that is greater than the external pressure by an amount greater than said predetermined pressure differential.

36. The method of claim 32, wherein the fluid is a liquid.

* * * * *